(12) United States Patent
Lindqvist et al.

(10) Patent No.: US 6,506,907 B1
(45) Date of Patent: Jan. 14, 2003

US006506907B1

(54) PROCESS

(75) Inventors: Bo Lindqvist, Södertälje (SE); Peter L. Sivertsen, Hörsholm (DK)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/600,325

(22) PCT Filed: May 9, 2000

(86) PCT No.: PCT/SE00/00913

§ 371 (c)(1),
(2), (4) Date: Jul. 14, 2000

(87) PCT Pub. No.: WO00/68193

PCT Pub. Date: Nov. 16, 2000

(30) Foreign Application Priority Data

May 11, 1999 (SE) .............................................. 9901712

(51) Int. Cl.$^7$ ............................................. C07D 205/04
(52) U.S. Cl. ........................................................ 548/953
(58) Field of Search ......................................... 548/953

(56) References Cited

U.S. PATENT DOCUMENTS

| | | | |
|---|---|---|---|
| 4,769,365 A | 9/1988 | Gellatly et al. | 514/210 |
| 4,847,409 A | 7/1989 | Kidman et al. | 562/401 |
| 4,870,189 A | 9/1989 | Lo et al. | 548/954 |
| 4,946,839 A | 8/1990 | Kozikowskip et al. | 514/210 |
| 5,136,050 A | 8/1992 | Martel et al. | 548/532 |
| 5,278,334 A | 1/1994 | Lin | 560/105 |
| 5,292,928 A | 3/1994 | Miltenberger | 560/226 |
| 5,880,291 A | 3/1999 | Ushio et al. | 548/953 |
| 6,150,535 A | 11/2000 | Awaji et al. | 548/950 |

FOREIGN PATENT DOCUMENTS

| | | |
|---|---|---|
| EP | 299 513 | 10/1994 |
| EP | 827 954 | 3/1998 |
| EP | 855 446 | 7/1998 |
| WO | 97/02241 | 1/1997 |
| WO | 97/41084 | 11/1997 |
| WO | 98/47867 | 10/1998 |

OTHER PUBLICATIONS

Wasserman et al. Preparation of B–Lactams from Azetidine–2–carboxylic Acids and Esters. Journal of Organic Chemistry. 46(15), 2991–2999, (1981).*
J. Heterocycl. Chem. 5(2), 309–311 (1968).
J. Heterocycl. Chem. 6(3), 435–437 (1969).
J. Heterocycl. Chem. 8, 19–24 (1971).
J. Heterocycl. Chem. 10, 795–799 (1973).
STN International, File CAPLUS, CAPLUS accession No. 1975:111176, Document No. 82:111176, Kostyanovskii et al. "N–alkyl–2–azetidine–carboxylates" (Izv. Akad. Nauk SSSR, Ser. Khim. 1975 (1), 119–124.
Biopolymers 30(11–12), 1039–1049 (1990).
Biochem. J. 64, 323 (1956).
Bull. Soc. Chem. Chim. France 4079 (1968).

* cited by examiner

*Primary Examiner*—Joseph K. McKane
*Assistant Examiner*—Rebecca Anderson
(74) *Attorney, Agent, or Firm*—Nixon & Vanderhye

(57) ABSTRACT

There is provided a process for the production of a N-benzyl azetidine-2-carboxylic acid alkylphenyl, or alkyl, ester which process comprises the reaction of an optionally substituted alkylphenyl, or an optionally substituted alkyl, 2-bromo-4-chlorobutyrate with an optionally substituted benzylamine, which process may be used as part of an overall process for the production of azetidine-2-carboxylic acid.

16 Claims, No Drawings

PROCESS

This application is a 371 of PCT/SE00/00913 filed May 9, 2000.

FIELD OF THE INVENTION

This invention relates to a novel process for the production of compounds which may be used in the production of azetidine-2-carboxylic acid (AzeOH).

PRIOR ART

L-Azetidine-2-carboxylic acid (L-AzeOH) is known to be useful in the synthesis of inter alia high molecular weight polypeptides and in particular as an analogue of the well known amino acid proline.

This amino acid is of limited availability from natural sources and consequently the development of an efficient and economic synthetic method for its production is desirable.

The formation of racemic AzeOH derivatives by cyclisation of halobutyric acid derivatives has been known for many years.

For example, Fowden (in Biochem. J. (1956) 64, 323) employed barium hydroxide and Duplan et al (in Bull. Soc. Chem. Chim. France (1968) 4079) employed sodium hydroxide to effect the cyclisation of 4-amino-2-halobutyric acids.

Similarly, the synthesis of racemic AzeOH benzyl ester derivatives from benzyl 2,4-dibromobutyrate was first reported by Phillips and Cromwell (in J. Heterocyclic Chem. (1973) 10, 795). In this publication, it is stated that 1-benzhydryl-2-AzeOH benzyl ester may be prepared by refluxing benzyl 2,4-dibromobutyrate in the presence of benzhydrylamine and spectral grade acetonitrile for 24 hours.

More recently, European patent application EP 827 954 discloses the formation of N-(alkylbenzyl)-AzeOH esters by reaction of butyric acid ester derivatives with optically-active alkylbenzylamines. The butyric acid esters are substituted at the 2- and 4-positions with leaving groups (such as halo). Benzyl, and certain alkyl, 2,4-dichlorobutyrates, as well as benzyl, and certain alkyl, 2,4-dibromobutyrates are specifically mentioned.

None of the above-mentioned documents describe the cyclisation of alkylphenyl, or alkyl, 2-bromo-4-chlorobutyrates in the presence of a benzylamine, so forming N-benzyl AzeOH alkylphenyl, or alkyl, esters. We have found that four-membered rings comprising the azetidine-2-carboxylate moiety may be obtained surprisingly efficiently, and in a surprisingly good yield, by way of just such a process.

DESCRIPTION OF THE INVENTION

According to a first aspect of the invention there is provided a process for the production of an optionally substituted N-benzyl AzeOH alkylphenyl, or alkyl, ester which process comprises the reaction of an optionally substituted alkylphenyl, or an optionally substituted alkyl, 2-bromo-4-chlorobutyrate with an optionally substituted benzylamine, which process is referred to hereinafter as "the process of the invention".

There is further provided a process for the preparation of a compound of formula I;

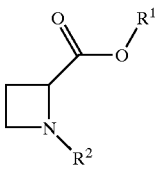

wherein
  $R^1$ represents optionally substituted lower alkyl or optionally substituted lower alkylphenyl; and
  $R^2$ represents optionally substituted benzyl,
which process comprises the reaction of a compound of formula II

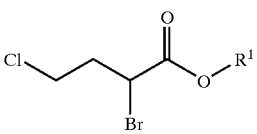

wherein $R^1$ is as defined above, with a compound of formula III, $R^2NH_2$        III wherein $R^2$ is as defined above.

Alkyl groups that $R^1$ may represent may be linear or branched. Suitable groups include linear or branched $C_{1-6}$ alkyl, especially $C_{1-4}$ alkyl groups such as t-butyl, n-propyl, i-propyl, ethyl and, especially, methyl groups.

Preferred alkylphenyl groups that $R^1$ may represent include optionally substituted $C_{1-3}$ alkylphenyl groups, such as optionally substituted benzyl groups. Alkylphenyl (including benzyl) groups that $R^1$ and $R^2$ may represent may be substituted on the alkyl part and/or on the phenyl part.

Optional substituents on $R^1$ and $R^2$ groups include halo (e.g. chloro and bromo), $C_{1-6}$ (e.g. $C_{1-4}$) alkyl (such as methyl), and $C_{1-6}$ (e.g. $C_{1-4}$) alkoxy (such as methoxy). Substituents on phenyl parts of alkylphenyl groups may be single or multiple and may be in any position relative to the alkyl part. Preferred points of substitution on phenyl rings include in the 4-position relative to the alkyl part. 4-Methoxy is an especially preferred substituent. Substituents on the alkyl parts of the alkylphenyl groups include, preferably, $C_{1-6}$ (e.g. $C_{1-4}$) alkyl, such as propyl, ethyl or methyl.

There is further provided a compound of formula I in which $R^1$ represents optionally substituted lower alkylphenyl (e.g. benzyl or 4-methoxybenzyl) and $R^2$ represents optionally substituted benzyl (e.g. benzyl or 4-methoxybenzyl).

There is further provided a compound of formula II in which $R^1$ represents optionally substituted lower alkylphenyl (e.g. benzyl or 4-methoxybenzyl).

The skilled person will appreciate that the process of the invention involves two consecutive reactions, the first an amination of a compound of formula II using a compound of formula III, the second a cyclisation of an aminated intermediate to form a compound of formula I. In this respect, an aminated intermediate of formula Ia:

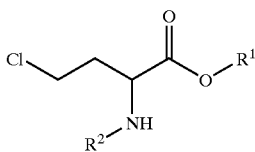

Ia wherein $R^1$ and $R^2$ are as hereinbefore defined may be isolated (or at least partially isolated) if desired. However, we prefer that the process of the invention is carried out as a one pot procedure.

The process of the invention may be carried out in an appropriate reaction solvent that does not interfere with the amination/cyclisation process. Appropriate reaction solvents include esters, such as ethyl acetate and iso-propyl acetate, ethers, such as tetrahydrofuran, polar aprotic solvents, such as acetonitrile, chlorinated solvents, such as dichloromethane, or mixtures thereof. Preferred solvents for the amination include polar aprotic solvents (especially acetonitrile), ethers (especially ethyl acetate and iso-propyl acetate). Preferred solvents for the cyclisation include polar aprotic solvents (especially acetonitrile).

The process of the invention may be carried out at an appropriate reaction temperature. Appropriate reaction temperatures for the amination are between room temperature (e.g. 20° C.) and the reflux temperature of the solvent that is employed. Appropriate reaction temperatures for the cyclisation are between 35° C. and the reflux temperature of the solvent that is employed, for example between 40° C. and reflux. In the case of a one pot process of the invention, in which the solvent that is employed is acetonitrile, preferred reaction temperatures are between 50° C. and reflux, especially reflux temperature, though the skilled person will appreciate that, even in a one-pot process, it is possible to initiate the reaction at or around room temperature and thereafter increase the temperature in order to promote the cyclisation.

The process of the invention may also be carried out in the presence of base, such as a carbonate of an alkali metal or an alkaline earth metal (e.g. potassium carbonate or calcium carbonate), and/or a catalyst, such as a source of iodine (e.g. an iodide of an alkali metal or an alkaline earth metal, such as sodium iodide or potassium iodide, or a quaternary ammonium iodide).

The process of the invention may be monitored using means that are well known to those skilled in the art. Appropriate reaction times will depend upon the degree and efficiency of conversion but are in the range 15 minutes to 48 hours, preferably 1 hour to 36 hours, more preferably 2 hours to 24 hours (for both the amination and cyclisation steps together, whether carried out separately or otherwise).

Appropriate concentrations of reactants, and proportion of reagents, may be determined readily by the skilled person. In any event, the skilled person will appreciate that reaction parameters, such as solvents, reagents, reaction times and reaction temperatures are interrelated, and will be able to devise and/or optimise appropriate parameters in accordance with routine techniques.

Work up, and isolation of compounds of formula I, may be carried out using routine techniques, such as those described hereinafter.

Compounds of formula II may be prepared for example by reaction of 4-chlorobutyryl chloride with bromine, followed by reaction of the brominated intermediate with an appropriate alkyl or alkylphenyl alcohol of formula IV, $R^1OH$     IV wherein $R^1$ is as hereinbefore defined. This reaction may advantageously be carried out in a one pot procedure, that is to say the brominated intermediate need not be isolated.

The bromination may be carried out by adding bromine directly to 4-chlorobutyryl chloride at an appropriate reaction temperature e.g. at or around 90 to 120° C., e.g. 100 to 110° C. The esterification may be carried out at or around room temperature, optionally in the presence of an appropriate reaction solvent that does not interfere with the reaction, such as a lower (e.g. $C_{6-12}$) alkane (e.g. heptane). Alternatively the alkyl alcohol of formula IV may be used as a solvent. This reaction may also optionally be carried out in the presence of a suitable base, such as sodium carbonate, sodium hydrogen carbonate, potassium hydrogen carbonate, sodium hydroxide, potassium hydroxide or, preferably, calcium carbonate or potassium carbonate. Appropriate reaction times for the bromination will depend upon the degree and efficiency of conversion but are in the range 1 to 5 hours, preferably 2 to 4 hours. Appropriate reaction times for the esterification will also depend upon the degree and efficiency of conversion but are in the range 2 to 20 hours, preferably 3 to 15 hours.

When alkyl and alkylphenyl 2-bromo-4-chlorobutyrates are prepared in this way, we have found, advantageously, that there is no need to purify (e.g. by distillation) the butyrate compound before performing a subsequent cyclisation step as described herein.

Compounds of formula I may be deprotected using standard deprotection techniques (e.g. hydrogenolysis in the presence of a suitable catalyst, by acid or base hydrolysis or by a combination of these methods, for example as described hereinafter), resulting in AzeOH, e.g. as the racemic compound.

The skilled person will appreciate that, if desired or required, transesterification reactions may be performed at certain stages in the overall route for the preparation of compounds of formula I, or indeed after such compounds have been formed. For example compounds of formulae I and II may be transesterified, once formed, to other compounds of formulae I and II respectively, using known techniques (e.g. as described hereinafter).

In particular, we have found that compounds of formula I in which $R^1$ represents optionally substituted benzyl may advantageously be deprotected in a one pot procedure, using standard deprotection techniques, such as those mentioned herein.

Compounds of formula I in which $R^1$ represents optionally substituted benzyl may be prepared directly by reacting a compound of formula II in which $R^1$ represents optionally substituted benzyl with a compound of formula III. Preferably, however, compounds of formula I in which $R^1$ represents optionally substituted benzyl may be prepared by reacting a compound of formula II in which $R^1$ represents lower alkyl (such as t-butyl, n-propyl, i-propyl, ethyl or, especially, methyl) with a compound of formula III, followed by transesterification of the resultant compound of formula I using standard techniques (e.g. using optionally substituted benzyl alcohol), for example as described hereinafter. We have found, surprisingly, that producing a compound of formula I in which $R^1$ represents optionally substituted benzyl in the latter way greatly facilitates the overall process and results in an improved impurity profile for the resultant compound.

AzeOH formed after a deprotection reaction may, if desired, be resolved to give enantiomerically-pure D- and/or, particularly, L-AzeOH, using known resolution techniques, for example as described in international patent applications WO 97/02241 or WO 97/41084, the disclosures in which documents are hereby incorporated by reference. By "enantiomerically-pure" AzeOH, we include any mixture of the enantiomers of AzeOH in which one enantiomer is present in a greater proportion than the other.

Thus, the process of the invention may be used as part of an overall synthesis for the production of AzeOH, D- and/or L-AzeOH, from 4-chlorobutyryl chloride. The AzeOH formed by way of the process of the invention may be utilised in a subsequent peptide coupling reaction. If enantiomerically-pure AzeOH is obtained by way of processes described in international patent applications WO 97/02241 and/or WO 97/41084, or by analogous processes, the skilled person will appreciate that it may be obtained by way of a diastereomerically-active tartrate salt. In such cases, enantiomerically-pure AzeOH need not be separately liberated/isolated before a subsequent coupling step is carried out.

The process of the invention has the advantage that it may be used in the production of AzeOH in a manner that means that the number of steps involved in the synthesis of the final compound is reduced.

Moreover, the process of the invention results in products (compounds of formula I) that are easy to extract, in a chemically pure form, from reaction solutions. Further, such product may be deprotected in situ (i.e. without the need to isolate it) to give AzeOH, in a manner that involves minimal loss of yield.

The process of the invention may also have the advantage that halogenated butyric acid derivatives may be cyclised to form four-membered rings comprising the azetidine-2-carboxylate moiety in higher yields, in higher chemical purity, in less time, more conveniently, at higher concentrations and at a lower cost, than when prepared via processes described in the prior art.

The invention is illustrated, but in no way limited, by the following examples.

EXAMPLE 1

Benzyl 2-bromo-4-chlorobutyrate (a) 2-Bromo-4-chlorobutyryl chloride

4-Chlorobutyryl chloride (282.0 g; 2.00 mol; Aldrich) was heated to 103° C. and bromine (352.0 g, 2.20 mol) was added over a period of 3 hours at 103–105° C. The mixture was stirred at 105° C. for an additional period of 1 hour and then cooled to room temperature. Nitrogen was passed through the mixture for a period of 1.5 hours and heptanes (1.5 L) were added. The mixture was concentrated via distillation at 60° C. under vacuum (down to 80 mmHg). GC analysis indicated completion of the bromination. The mixture containing sub-title product was used directly in the next step.

(b) Benzyl 2-bromo-4-chlorobutyrate

Heptanes (1.5 L) and calcium carbonate (150 g; 1.50 mol) were added to the distillation residue from step (a) above and benzyl alcohol (236.8 g; 2.19 mol) was added with stirring at 23–25° C. After stirring for 3.5 hours at 23–25° C., GC analysis indicated approximately 20% of unreacted acyl chloride. After additional stirring for 20 hours, approximately 10% of unreacted acyl chloride was estimated to be present by GC. The resultant mixture was filtered, and the filter cake was washed with heptanes (600 mL). Tetrahydrofuran (200 mL) and a 6% aqueous sodium hydrogen carbonate solution (400 mL) were added to the combined filtrates, and the mixture was stirred for 1 hour at room temperature. The aqueous phase (pH approximately 1) was separated and discarded. The organic phase was washed with water (400 mL) and concentrated at 60° C. under vacuum (down to 25 mmHg). GC analysis on the residue (497.7 g; 85% yield), indicated approximately 7% of unreacted acyl chloride. The hydrolysis of unreacted starting material was forced to completion by addition of further heptanes (1.52 L), tetrahydrofuran (150 mL) and 6% aqueous sodium hydrogen carbonate (600 mL). After stirring for 1 hour at room temperature, less than 1% unreacted acyl chloride was estimated to be present by GC. The aqueous phase (pH approximately 8) was separated and discarded. The organic phase was washed with water (200 mL) and concentrated at 65° C. under vacuum (down to 25 mmHg). This resulted in 418.1 g (72%) of crude title compound as a tea coloured residual oil.

Purity (GC) 87.7%

$^{13}$C NMR (300 MHz; CDCl$_3$ (77.0)): $\delta$36.8 (C-3), 41.6 (C-4), 42.5 (C-2), 67.8 (C-benzyl), 128.2, 128.57, 128.63, 134.9 (Ph), 168.95 (CO$_2$Bn)

EXAMPLE 2

N-Benzyl-D,L-AzeOH benzyl ester

Benzylamine (152.0 g; 1.42 mol) was added to a solution of benzyl 2-bromo-4-chlorobutyrate (413.4 g; 1.42 mol; from Example 1 above) in acetonitrile (2.8 L) and the mixture was heated under reflux (81° C.) for 1 hour. After refluxing for 1 hour, GC analysis indicated approximately 50% of unreacted starting material was present. The mixture was then cooled to 45–50° C. and potassium carbonate (391.9 g; 2.84 mol) was added over a period of 5 minutes. Sodium iodide (106.3 g; 0.71 mol) was then added, and the suspension heated to reflux. The mixture was heated under reflux overnight, after which more than 98% conversion to the title compound was estimated by GC. The suspension was cooled to room temperature and filtered. The filter cake was washed with acetonitrile (1200 mL) and the combined filtrates were concentrated through distillation at 60° C. under vacuum (down to 10 mmHg). Heptanes (2.5 L), toluene (475 mL) and water (1.4 L) were added to the residual mixture of oil and crystals. The mixture was heated to 46–48° C. with stirring and then left for phase separation. The aqueous phase was discarded. Water (1.5 L) and methanol (550 mL) were added to the organic phase and the pH was adjusted to 2.2 through the addition of 6N aqueous sulfuric acid (220 mL; 1.32 mol). The mixture was stirred at 46–48° C. and left for phase separation. The aqueous phase was separated and the organic phase was extracted twice at 46–48° C. with a mixture of water (500 mL) and methanol (100 mL). The organic phase was discarded including a small amount of separated oil (containing mainly impurities). Toluene (1.5 L) was added to the combined aqueous phases (3.8 L), and the pH was adjusted to 4.8 through the addition of solid potassium carbonate (80.8 g; 0.58 mol). The organic phase was separated and the turbid aqueous phase was extracted twice with toluene (500 mL each). The combined organic phases were washed with water and concentrated as much as possible at 70° C. under vacuum (down to 25 mmHg). The title compound (277.4 g; 70%) was thus isolated as a residual yellow oil. GC indicated a purity of 98.0%. The crude product was purified by adding toluene (1000 mL), heptanes (1500 mL) and water (2.250 ML) to the oil. 5% w/w of aqueous hydrogen peroxide (500 mL) was then added and the mixture stirred for 10 minutes at room temperature. The pH was then adjusted to 2.1 through the addition of 3N aqueous hydrochloric acid (275 mL; 0.83 mol). The aqueous phase was separated and the organic phase was washed with water (500 mL). Toluene (1800 mL) was added to the combined aqueous phases and the pH adjusted to 4.8 through addition of 10% w/w aqueous potassium carbonate (516.2 g; 0.37 mol). The organic phase was separated and the turbid aqueous phase extracted with toluene (600 mL). The combined organic extracts were concentrated at 70° C. under vacuum (down to 20 mmHg). 196.5 g (80%) of purified title compound was isolated.

$^{13}$C NMR (300 MHz; CDCl$_3$ (77.0)): δ21.5 (C-3), 50.8 (C-4), 62.3 (C-2), 64.3, 66.2 (C-benzyl), 127.2, 128.1, 128.2, 128.5, 128.7, 129.0, 135.7, 137.0 (Ph), 172.35 (CO$_2$Bn)

EXAMPLE 3

Methyl 2-bromo-4-chlorobutyrate

4-Chlorobutyryl chloride (527 g) was heated to 105° C. and bromine (232 mL) was added slowly over a period of 3 hours. The reaction was heated for an additional 0.5 hours, cooled down to 20° C. and was then added to stirred methanol (3.5 L, 15–17° C.), keeping the reaction temperature below 30° C. The reaction was left overnight at 21° C. The methyl ester solution was cooled to 15° C. and 25% (w/w) K$_2$CO$_3$(aq.) (1 L) was added, keeping the temperature below 25° C. Methanol was evaporated from the obtained mixture and iso-propyl acetate (2.2 L) was added. The precipitated salt was dissolved by adding water (350 mL) and the pH was adjusted to pH 8.5–9 with 25% K$_2$CO$_3$(aq). The water phase was discarded. The organic layer was washed once with 15% (w/w) NaCl(aq) (300 mL) and then evaporated. To the remaining liquid product (720 g; 90%), iso-propyl acetate (1.5 L) was added, to give 2.9 L of an approximately 25% (w/w) product solution.

Purity 98.0% (GC)

MS (EI): m/z 183 (M−31)$^+$, 152 (M−CH$_2$CHCl)$^+$

EXAMPLE 4

Methyl N-benzylazetidine-2-carboxylate (a) Methyl 2-(benzylamino)-4-chlorobutyrate and Methyl N-benzylazetidine-2-carboxylate To a 2 L reactor, a 25% (w/w) solution of the methyl 2-bromo-4-chloro-butyrate in iso-propyl acetate (see Example 3; corresponding to 147 g of 100% methyl 2-bromo-4-chlorobutyrate) was added and diluted with iso-propyl acetate (600 mL). K$_2$CO$_3$(s) (155.5 g, 1.11 mol) was added under vigorous stirring at 20° C., followed by benzylamine (150.4 g, 1.40 mol). The mantle temperature of the reaction vessel was programmed to reach 55° C. over 1.5 h, then switching to reaction temperature control, set on 55° C. After approximately 20 h, the reaction was cooled down. At 15° C., water (450 mL) was added, dissolving the potassium salts, and the water phase was discarded. Further water (375 mL) was added and the mixture was acidified to pH~5.5 with 32% (w/w) HCl(aq) (35 L). At 20° C., the water phase was separated off and extracted once with iso-propyl acetate (100 mL). The combined organic phases were washed once with 15% (w/w) NaCl(aq) (160 mL). Evaporation of the solvent gave a yellowish liquid, 223.2 g (purity (GC) 81.7 area % as a mixture of methyl 2-(benzylamino)-4-chlorobutyrate and methyl N-benzylazetidine-2-carboxylate. The calculated yield of methyl 2-(benzylamino)-4-chlorobutyrate and methyl N-benzylazetidine-2-carboxylate was around 95%. The liquid was used as such in the next step.

(b) Methyl N-benzylazetidine-2-carboxylate

To a 2 L reactor with 155.8 g of the liquid from step (a) above, acetonitrile (1.4 L) was added. K$_2$CO$_3$(s) (97.6 g) was added with vigorous stirring at 20° C. followed by KI (14.9 g). The reaction was heated at reflux for about 24 h. After cooling to 20° C., the slurry was filtered and the filter cake was washed with acetonitrile (3×100 mL). The combined filtrates were evaporated, iso-propyl acetate (400 ML) was added and the mixture was evaporated once more. The obtained mixture was partitioned between iso-propyl acetate (600 mL) and 15% (w/w) brine (150 mL) and the water phase was discarded. The organic layer was washed once more with 15% (w/w) brine (100 mL). To the obtained crude product solution, iso-propyl acetate (700 mL) and water (800 mL) were added and pH was adjusted to 2.35 with 1M H$_2$SO$_4$. After separation, the organic layer was extracted once more with water (50 mL) and the combined water phases were washed with iso-propyl acetate (2×50 mL). To the acidic water phase, iso-propyl acetate (1.75 L) was added and methyl N-benzylazetidine-2-carboxylate was extracted at pH 8.9 by addition of solid K$_2$CO$_3$ (59.5 g). The water phase was discarded and the organic layer was washed with 15% (w/w) brine (100 mL). The organic phase was evaporated to give methyl N-benzylazetidine-2-carboxylate as a bright brown-yellowish liquid in 82% yield (purity(GC) 89.8 area % ).

MS (EI): m/z 205 (M)$^+$, 190 (M−15)$^+$, 177 (M−CH$_2$CH$_2$)$^+$, 146 (M−59)$^+$

EXAMPLE 5

Benzyl N-benzylazetidine-2-carboxylate

To 68.3 g of methyl N-benzylazetidine-2-carboxylate (see Example 4 above; purity 89.8 area % ), acetonitrile (127 mL), K$_2$CO$_3$(s) (23.3 g) and benzyl alcohol (75.6 g) were added. The stirred reaction slurry was heated to between 75 and 80° C., and a modest vacuum (p>700 mbar) was applied. Methanol and acetonitrile were distilled off and, as the reaction slurry became highly concentrated, more acetonitrile was added and the distillation was continued. This procedure was repeated until a conversion of 97% was attained. The concentrated reaction mixture was cooled to 20° C. and diluted with acetonitrile (70 mL). The solid salts were filtered off and the filter cake was washed with acetonitrile (3×50 mL). The solvent was evaporated off at 40° C. To the remaining high-boiling liquid, heptane (1.5 L) and 5% (w/w) NaCl(aq.) (700 mL) were added, giving a mixture of three phases. 2 M H$_2$SO$_4$ (5 mL) was added to give a pH of about 8. After two more extractions of the organic phase with 5% (w/w) NaCl (aq), and water at pH 8, almost all of the third phase (benzyl alcohol) was successfully dissolved. Water (550 mL) was added to the organic phase and the pH was adjusted to 2.6 with 2M H$_2$SO$_4$ (38 mL). After separation, the organic phase was extracted with two more portions of acidified water (150 mL H$_2$O at pH 2.2, followed by 50 mL H$_2$O at pH 2.6). The organic phase was discarded. To the combined aqueous phases (pH 2.5), heptane (1.25 L) was added and pH was adjusted to 4.5 with K$_2$CO$_3$(s). The organic phase was separated off and washed with 10% (w/w) NaCl (aq.) and water. The obtained organic phase was evaporated at 40° C., until a bright yellow to brownish liquid remained (65.1 g, according to titration 94.0% (w/w)

product, 4.3% (w/w) benzyl alcohol, purity(GC) 99.5 area %). A second crop of product was isolated as above by extracting the remaining water phase (pH 4.5) with three more portions of heptane (0.25/0.1/0.1 L heptane at pH 5.8/5.2/4.9). Yield 7.8 g of a slightly more coloured product (assay 90% (w/w) according to titr., purity(GC) 97.9 area %), resulting in a total yield of 87% (68.2 g, 0.242 mol).

MS (El): m/z 280 (M−1)$^+$, 190 (M−91)$^+$, 146 (M−CO$_2$Bn)$^+$

EXAMPLE 6

Azetidine-2-carboxylic acid

Hydrogenation was carried out on the resultant pure title compound of Example 2 above (70.35 g; 250 mmol) in acetic acid (700 mL), using palladium on carbon catalyst. After hydrogenation was complete, the catalyst was filtered off, and the filtrates were concentrated resulting in a mixture containing a theoretical amount of 25.25 g D,L-AzeOH. Acetic acid was added to the residue, resulting in a 13.5% w/w solution of D,L-AzeOH in acetic acid. A D-tartaric acid resolution was carried out on 5.05 g (50 mmol) of D,L-AzeOH, in analogous fashion to procedures described in international patent application WO 97/41084, yielding 8.05 g (64%) of crude L-AzeOH-D-tartrate with a diastereomeric excess of 95.8%. The crude salt was recrystallised from aqueous ethanol, yielding 6.28 g of pure L-AzeOH-D-tartrate as white crystals. HPLC indicated a diastereomeric excess of 100%.

What is claimed is:

1. A process for the production of an optionally substituted N-benzyl azetidine-2-carboxylic acid alkylphenyl, or alkyl, ester which process comprises the reaction of an optionally substituted alkylphenyl, or an optionally substituted alkyl, 2-bromo-4-chlorobutyrate with an optionally substituted benzylamine, wherein the reaction is carried out in the presence of a catalyst.

2. A process as claimed in claim 1 wherein the N-benzyl azetidine-2-carboxylic acid ester is of formula I:

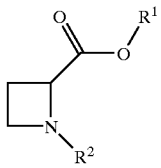

wherein

R$^1$ represents optionally substituted lower alkyl or optionally substituted lower alkylphenyl; and R$^2$ represents optionally substituted benzyl, and the process comprises the reaction of a compound of formula II:

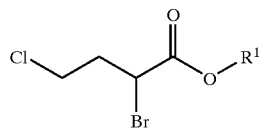

wherein R$^1$ is as defined above, with a compound of formula III,

wherein R$^2$ is as defined above.

3. A process as claimed in claim 2 wherein R$^1$ represents linear or branched C$_{1-6}$ alkyl or C$_{1-3}$ alkylphenyl, which alkylphenyl group is optionally substituted by halo, C$_{1-6}$ alkyl or C$_{1-6}$ alkoxy.

4. A process as claimed in claim 3 wherein R$^1$ represents t-butyl, n-propyl, i-propyl, ethyl, methyl, benzyl or 4-methoxybenzyl.

5. A process as claimed in claim 2, wherein R$^2$ is optionally substituted by halo, C$_{1-6}$ alkyl or C$_{1-6}$ alkoxy.

6. A process as claimed in claim 5, wherein R$^2$ represents benzyl or 4-methoxybenzyl.

7. A process as claimed in claim 1 or 2 which is carried out as sequential amination and cyclisation reaction in one pot.

8. A process as claimed in claim 2 in which an aminated intermediate of formula Ia,

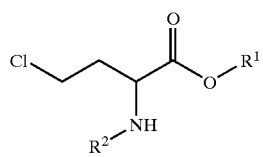

wherein R$^1$ and R$^2$ are as defined in claim 2 (as appropriate), is at least partially isolated.

9. A process as claimed in claim 1 or 2, wherein the reaction is carried out in the presence of one or more of ethyl acetate, tetrahydrofuran, iso-propyl acetate, dichloromethane and acetonitrile as solvent.

10. A process as claimed in claim 9, wherein the solvent is acetonitrile and/or iso-propyl acetate.

11. A process as claimed in claim 1 or 2, wherein the reaction is carried out at between 50° C. and reflux temperature.

12. A process as claimed in claim 11, wherein reaction is carried out at reflux temperature.

13. A process as claimed in claim 1 or 2, wherein the reaction is carried out in the presence of base.

14. A process as claimed in claim 13, wherein the base is potassium carbonate or sodium carbonate.

15. A process as claimed in claim 1 or 2, wherein the catalyst is sodium iodide or potassium iodide.

16. A process as claimed in claim 1 or 2, wherein the reaction is carried out for between 15 minutes and 48 hours.

* * * * *